United States Patent [19]

Mathiowitz et al.

[11] Patent Number: 5,912,017
[45] Date of Patent: Jun. 15, 1999

[54] MULTIWALL POLYMERIC MICROSPHERES

[75] Inventors: Edith Mathiowitz, Brookline; Robert S. Langer, Newton, both of Mass.

[73] Assignee: Massachusetts Institute of Technology, Cambridge, Mass.

[21] Appl. No.: 07/906,403

[22] Filed: Jul. 1, 1992

Related U.S. Application Data

[63] Continuation of application No. 07/603,913, Oct. 24, 1990, abandoned, which is a continuation of application No. 07/348,795, May 8, 1989, abandoned, which is a continuation-in-part of application No. 07/045,840, May 1, 1987, Pat. No. 4,861,627.

[51] Int. Cl.$^6$ .............................. A61K 09/52; B01J 13/12
[52] U.S. Cl. ......................... 424/494; 424/486; 424/497; 427/213.31; 427/213.36; 428/402.22; 428/402.24; 514/963; 514/965
[58] Field of Search ......................... 428/402.22, 402.24; 424/462, 463, 486, 493, 496, 497, 494; 514/963, 965

[56] References Cited

U.S. PATENT DOCUMENTS

| | | | |
|---|---|---|---|
| 3,523,906 | 8/1970 | Vrancken et al. | 264/4.6 |
| 3,640,892 | 2/1972 | Purcell | 264/4.6 |
| 3,691,090 | 9/1972 | Kitajima et al. | 264/4.6 |
| 3,830,750 | 8/1974 | Wellman | 264/4.6 |
| 3,859,228 | 1/1975 | Morishita et al. | 427/213.36 |
| 3,960,757 | 6/1976 | Morishita et al. | 427/213.36 |
| 4,187,194 | 2/1980 | Wellman et al. | 264/4.6 |
| 4,263,273 | 4/1981 | Appelgren et al. | 424/494 |
| 4,272,398 | 6/1981 | Jaffe | 427/213.31 |
| 4,303,638 | 12/1981 | Tayot et al. | 424/490 |
| 4,622,244 | 11/1986 | Lapka et al. | 424/497 X |
| 4,637,905 | 1/1987 | Gardner | 264/4.3 |
| 4,756,907 | 7/1988 | Beck et al. | 424/85 |
| 4,861,627 | 8/1989 | Mathiowitz et al. | 427/213.31 |

OTHER PUBLICATIONS

Mathiowitz et al., *J. Appl. Polymer Sci.* 26, 809–822 (1981).
Mathiowitz et al., J. Controlled Release 5, 13–22 (1987).
Mathiowitz et al., *Proceedings International Symposium of Controlled Release by Active Material* 12, 183–184 (Jul. 1985).

*Primary Examiner*—Richard D. Lovering
*Attorney, Agent, or Firm*—Arnall Golden & Gregory, LLP

[57] ABSTRACT

A method for preparation of multi-layer polymeric microspheres formed from any degradable or non-degradable polymers which are not soluble in each other at a particular concentration, but which have a positive spreading coefficient in solution. The multi-layer microspheres produced by the method are distinguished by extremely uniform dimensioned layers of polymer and actual incorporation of the substance to be delivered into the polymer layers. In the preferred embodiment of the method, two polymers are dissolved in a volatile organic solvent, the substance to be incorporated is dispersed or dissolved in the polymer solution, the mixture is suspended in an aqueous solution and stirred, and the solvent is slowly evaporated, creating microspheres with an inner core formed by one polymer and an outer layer formed by the second polymer. In another embodiment, solvent is removed by spray drying. In still another embodiment, polymers are melted and combined with the substance to be incorporated, then cooled to form layered microspheres.

5 Claims, 3 Drawing Sheets

MULTIWALL POLYMERIC MICROSPHERES

This application is a continuation of Ser. No. 07/603,913 filed Oct. 24, 1990, now abandoned, which is a continuation of Ser. No. 07/348,795 filed May 8, 1989, now abandoned, which is a continuation-in-part of Ser. No. 07/045,840 filed May 1, 1987, now U.S. Pat. No. 4,861,627.

The United States Government has certain rights in this invention pursuant to National Institute of Health Grant No. NIH-5-RO1-GM26698.

BACKGROUND OF THE INVENTION

This is a method for preparing multiwall polymer microspheres, particularly for use in controlled delivery systems.

Controlled delivery of substances, for example, drugs, insecticides, fertilizers, and indicators, can be accomplished using a variety of processes. In one type of delivery system, a polymeric capsule is formed around or incorporating the substance to be delivered. The form and composition of the polymer or polymers determines the method that can be used to incorporate the substance, the environment in which the capsule can be used, and the type of substance which can be incorporated.

One process for preparing microspheres is a hot-melt technique. The melted polymer is mixed with the drug and the mixture suspended in a non-solvent where it is cooled and solidified. The big disadvantage of this process is that only low melting polymers can be used with thermolabile substances.

An alternative method is the solvent evaporation technique, disclosed, for example, by U.S. Pat. No. 3,523,906 to M. N. Vrancken and U.S. Pat. No. 3,960,757 to M. Morishita. These processes have been used extensively to prepare microspheres from biodegradable polymers, as reported in the literature and by H. Jaffe in U.S. Pat. No. 4,272,398. The procedure generally consists of dissolving a polymer in methylene chloride or other volatile solvent, dissolving or suspending a drug in the solution and emulsifying the resulting mixture in an aqueous phase containing an emulsifier. The solvent is then evaporated to produce microspheres containing the substance to be incorporated. The technique of Morishita dissolves a hydrophobic polymer in an organic solvent which is poorly miscible with water and has a boiling point less than water. A substance is dissolved in the polymer solution, the solution emulsified in an aqueous solution of a hydrophilic colloid or surface active agent, and the organic solvent removed by evaporation.

Yet another method used to form microcapsules is phase separation. Essentially, a polymer is forced to precipitate around a core by addition of non-solvent or by addition of a second polymer which is incompatible with the first polymer.

While all of these methods are useful in making microspheres for controlled delivery, they have certain disadvantages. For example, they do not always yield uniform polymer layers. The best one can do at present is to dip microspheres formed of one polymer into a bath of a second polymer and hope each microsphere is coated. In practice, the coatings tend to be non-uniform both with respect to coverage and to thickness. This can be fatal to a system for controlled delivery, as in controlled drug delivery systems requiring linear release of the drug as the polymer degrades in vivo. Further, many of these methods require multiple steps, with increasing quality control problems at each stage. The final yield is frequently low.

Even the fluidized bed method of forming a polymer coating around tablets, where uniform coatings are achievable, has disadvantages. Here, the substance to be incorporated cannot be mixed directly into the coating, especially when the substance is in particle form.

It is therefore an object of the present invention to provide a one step method for manufacturing delivery systems consisting of polymer layers in microspheres form.

It is a further object of the present invention to provide a method for manufacturing polymeric devices from a variety of polymers, including both biodegradable and non-biodegradable polymers.

It is another object of the present invention to provide a method for making polymeric delivery devices where substances in particle form can be incorporated directly into the polymers and which can be conducted at relatively low temperatures to avoid damaging any thermolabile substances to be incorporated.

SUMMARY OF THE INVENTION

A method for making multilayer polymeric microspheres for delivery of an incorporated substance, and the product thereof, microspheres with well defined, distinct, concentric polymeric layers. Polymer solutions are prepared by selecting two or more polymers which form separate and distinct phases when placed in a given solvent system or melted. The separation of the polymers can be predicted based on measurements of the surface tension or interfacial tension and calculation of the spreading coefficients for each polymer. The polymer and solvent systems are then selected which result in complete engulfment of one polymer by the other.

In the preferred embodiment of the method, two polymers which are immiscible in each other are dissolved in a volatile organic solvent which will yield the desired result based on interfacial tension and spreading coefficients of the polymers in solution, the drug is dispersed or dissolved in the polymer solution, the mixture is suspended in an aqueous solution and stirred, and the solvent is slowly evaporated, creating microspheres with an inner core formed by one polymer and an outer layer of the second polymer.

In another embodiment, each of the polymers is dissolved in different organic solvents and then mixed together. Polymer-solvent systems that are not soluble in each other are selected so that a suspension or emulsion is produced. This suspension or emulsion is then suspended in a third solvent in which neither of the first two polymer-solvent systems is soluble. Multiwall microspheres are formed when the solvents are evaporated and the polymer with the lower surface tension is engulfed by the other polymer.

In yet another embodiment, the solvents are evaporated rapidly to produce spheres of the first polymer within a layer of the second polymer, using a technique such as spray drying. The rate can be varied to form layers of each polymer with spheres within one polymer layer or to have all of one polymer in the form of spheres within the layer of the second polymer.

In still another embodiment, two or more polymers are melted, blended together, and suspended in a non-solvent for both polymers. Based on the spreading coefficients, one polymer will engulf another to form multilayered microspheres.

The important parameters for producing multi-layered capsules of the desired composition are: the selection of the polymers, including the purity and the molecular weights of the selection, the solvent, the solubility and concentration of the polymers in the solvent, the-selection and composition of the non-solvent, including the addition of an emulsifier to the non-solvent, the processing temperature, the rate of solvent evaporation, the rate of mixing, and the physical and chemical properties of the substance to incorporated. The optimum conditions can be determined empirically by one skilled in the art by measuring the surface tension or interfacial tension of the polymers under the processing conditions.

Examples demonstrate the production of multi-layered microspheres composed of polystyrene and ethylene vinyl acetate, polyanhydride and polystyrene, and polyanhydride and polylactic acid.

DETAILED DESCRIPTION OF THE INVENTION

Figure 1:
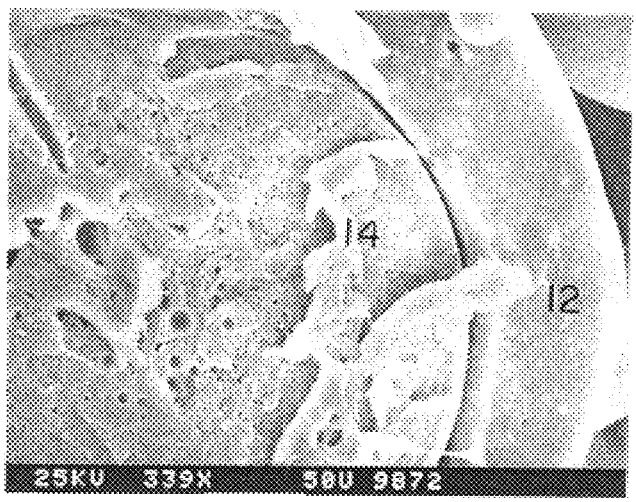
FIG. 1 is a photomicrograph of a microsphere having a polystyrene layer and an ethylene vinyl acetate layer, in cross-section, made according to the method of the present invention.

The method of the present invention is described in detail as follows.

Selection of polymer

Any polymer can be used in the method described herein. The polymers are selected on the basis of their physical and chemical properties, including their degradation characteristics in vivo when used in biomedical applications. Factors which must be taken into consideration in the selection of the polymer include the purity of the polymer, its molecular weight, and its solubility in organic and inorganic solvents. Polymers must be immiscible in each other.

Preferred biodegradable polymers are polyanhydrides; such as poly[bis(p-carboxy-phenoxy)propane anhydride] (CPP) copolymerized with sebacic acid (SA), (pCPP:SA, 20:80) and (pCPP:SA, 50:50) and CPP copolymerized with dodecanedoic acid (DD), (pCPP;DD, 20:80) and (pCPP:DD, 50:50), and other similar copolymers, polyglycolic acid, polylactic acid, polyorthoesters, polybutadiene, ethylene vinyl acetate, and copolymers and blends thereof. Polyanhydrides display surface erosion and linear release in vivo. Polylactic acid rapidly degrades in vivo after a relatively long lag period. Polyorthoester is particularly resistant to degradation in vivo. Ethylene vinyl acetate has been approved by the FDA for use in vivo. Useful polymers include ethyl cellulose and other enteric coating materials.

Preferred non-degradable polymers include polystyrene, polybutadiene, polyurethane, and polyamide.

Polymers can be liquified either by melting the polymers or by dissolving the polymers in one or more solvent systems. The most important criteria for determining which polymer systems will form multilayer microspheres is the interfacial tension of the liquified polymers and the spreading coefficient for the polymer system. As described in the examples, interfacial tension can be measured, calculated from surface tension, which can also be measured, or determined from the published literature. The spreading coefficient of the polymer system is calculated from the interfacial tension. When the spreading coefficient is positive, one polymer will engulf the other.

Selection of the Solvents

The solvents must be chosen in conjunction with the polymers so that the polymers to be incorporated into the microspheres will initially go into solution and then separate into distinct phases, with one polymer being engulfed by another. The solvents must also be easily evaporated when non-solvent is added to the polymer-solvent mixture. Most of the polymers can be dissolved in a volatile organic solvent such as methylene chloride. The choice of solvent will also be dependent on the substance to be incorporated into the polymers since some may have a detrimental effect on biological activity.

Selection of the Substance to be Incorporated

Examples of substances which can be incorporated include drugs, fertilizers, insecticides, chemical indicators or dyes, chemical reactants and scents or flavorings. Drugs which can be delivered by means of the present invention include insulin and heparin. The substance to be incorporated must not be adversely affected by the polymer solvent or the temperature at which solvent evaporation occurs. It is preferably provided in solution or in a particle size small enough to avoid "channeling" within the polymer, although it can also be provided in a suspension. This is generally in the range of 50 microns or less. The substance can be soluble in the organic solvent. Purity and molecular weight of the substance, as well as its solubility in the polymer solutions, are factors to consider in optimizing the method.

Mixing of the Polymer Solutions with the Substance to be Incorporated

The polymers may be combined with the substance to be incorporated in either of two ways. In one method, each polymer is dissolved or melted separately and the solutions combined. In the second, both polymers are simultaneously dissolved in one volatile organic solvent. The ultimate dispersion of the substance within the polymeric microspheres is determined in part by the method of dissolution and combination. The substance to be incorporated can be added directly to one or both of the polymer solutions or to the mixture.

The polymers are mixed together using conventional means such as an overhead stirring device. The rate of stirring has an effect on the formation of the polymer layers and should be optimized for each polymer-solvent mixture.

Suspension of Polymer Solution in a Non-Solvent

In the preferred embodiment, the polymer solution is suspended in a non-solvent, preferably an aqueous solution containing between 0 and 10% surface active agent, most preferably between 1 and 2% surface active agent. Useful surface active agents include polyvinyl alcohol, gelatin, and other surfactants and emulsifiers known to those skilled in the art.

There are three principal methods by which the hardened microspheres are formed.

a. Removal of Solvent by Evaporation

The solvent(s) are slowly evaporated using methods known to those skilled in the art, such as vacuum evaporation, lyophilization, or solvent evaporation in a non-solvent. Temperatures of between $-20°$ C. and $60°$ C. are preferred due to the labile nature of many drugs with biological activity.

The polymer suspension can be frozen after one polymer has engulfed the other to stabilize the microspheres during solvent removal.

b. Removal of Solvent by Spray Drying

It is possible to form the desired microspheres by spray drying the polymer solution containing the substance to be incorporated. A key factor here is to dry the spheres rapidly enough for the engulfing polymer to completely coat the polymer with the lower surface tension.

It is critical to control the rate of evaporation, as well as the parameters previously discussed, for one polymer solution to form a layer around a core of another polymer solution. However, the effect of the rate of evaporation on polymer layer formation may be used to advantageously modify the final product. For example, increasing the rate of evaporation can cause the formation of spheres of the first polymer within the second polymer layer. By increasing the rate of evaporation still further, no inner layer is formed and all of the first polymer is present in spherical form within the second polymer layer. The inclusion of the spheres may be useful in forming "channels" of a biodegradable polymer such as polyanhydride within an outer layer of a non-degradable polymer such as polystyrene.

c. Cooling of mixtures of melted polymers

When two melted polymers in a non-solvent which have a positive spreading coefficient are rapidly cooled, multi-layer microspheres can be formed. The rate of cooling is important to formation of microspheres having complete, uniform layers of polymer.

Additional Polymer Layers

Although more than two polymers can be layered using the above techniques, the complexity of the process dramatically increases with each additional polymer. It is therefore preferred to add other layers using methods known to those skilled in the art such as the hot-melt technique.

The present invention is further described by the following non-limiting examples.

EXAMPLE 1

Preparation of Polystyrene-Ethylene vinyl Acetate Microspheres

One g of polystyrene was dissolved in 5 ml methylene chloride. 1 g of ethylene vinyl acetate (EVA) was dissolved in 5 ml methylene chloride. The two solutions were mixed together, suspended in an aqueous solution, and the solvent evaporated. Two well-defined layers appear which are the result of one polymer solution engulfing the other. After 5 hours the microspheres were washed and dried. FIG. 1 is a cross-sectional view of one of the resulting microspheres 10 having a well-defined outer layer 12 and an inner layer 14.

EXAMPLE 2

Preparation of Polystyrene-Polyanhydride Microspheres

Figure 2:
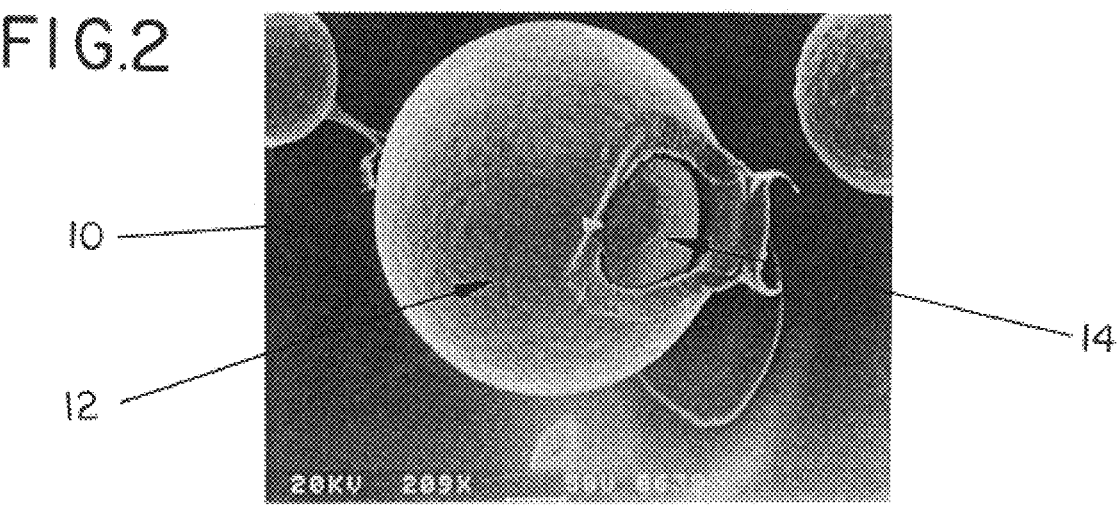
FIG. 2 is a perspective photomicrograph of microspheres having a polyanhydride layer and a polystyrene layer, made according to the method of the present invention.

The same method was used as in Example 1 with polystyrene and polyanhydride as the polymers. As shown in FIG. 2, the resulting microspheres 10 consist of an inner core 14 and outer layer 12. As determined by infrared spectroscopy, the internal core 14 consists of the polyanhydride.

EXAMPLE 3

Preparation of Polylactic Acid-Polyanhydride Polymers

Figure 3:
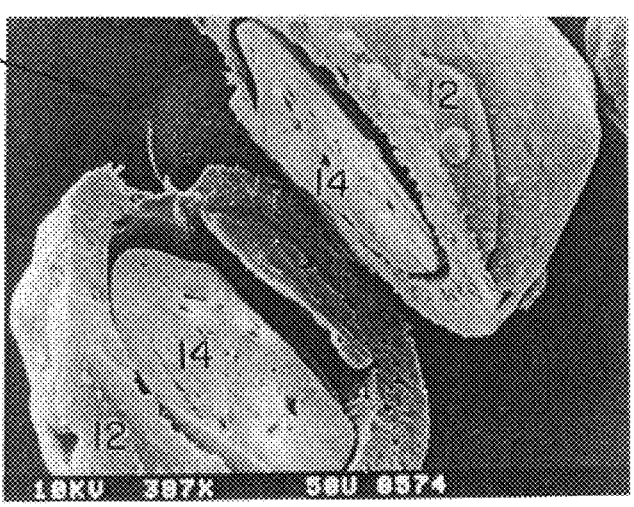
FIG. 3 is a photomicrograph of a microsphere having a polylactic acid layer and a polyanhydride layer, in cross section, made according to the method of the present invention.

The same method was again used but with polylactic acid and polyanhydride polymers. Methyl red was dispersed within both polymers. The resulting microspheres 10 having an internal layer 14 and outer layer 12 are shown in cross-section in FIG. 3.

Figure 4:
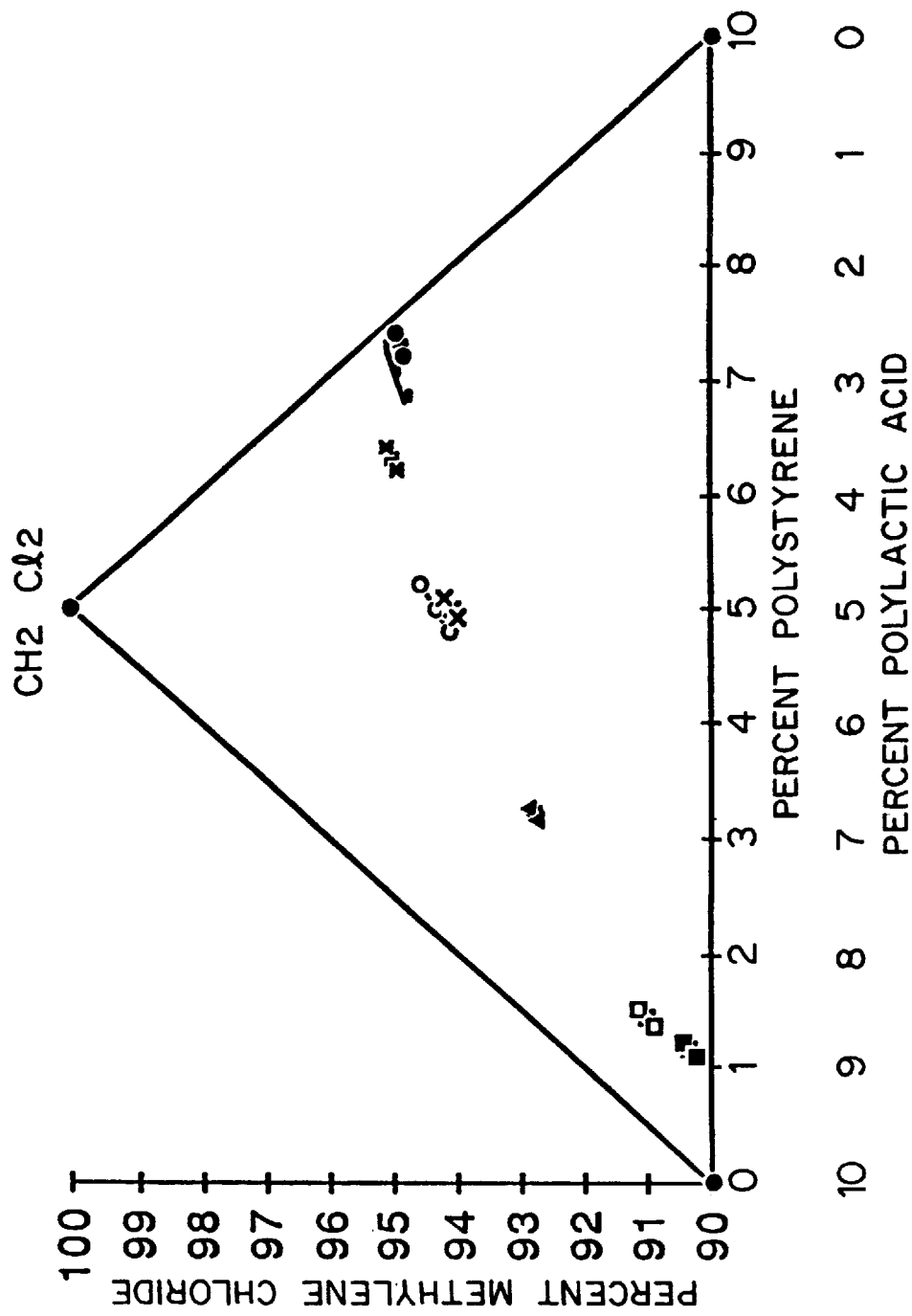
FIG. 4 is a phase diagram of the percent methylene chloride versus the percent polylactic acid and percent polystyrene in a methylene chloride mixture, where the relative percentages within the area below the curve are at the ratios which separation of the polymers occurs.

The separation of the two polymer phases is predicted on the basis of the phase diagram for the two polymers in the solvent. When the polymers are at a ratio underneath the separation curve for the polymer-solvent mixture, the polymers form distinct phases. The phase diagram for polystyrene-polylactic acid polymers in methylene chloride is shown in FIG. 4. Experimental data is plotted for mixtures of polystyrene with polylactic acid in methylene chloride. Separation into two distinct phases occurred in all cases. Since the relative ratios are all under the separation curve, one is assured of obtaining two separate layers of polymers.

One can determine whether one polymer will completely engulf the other polymer by determining the surface and/or interfacial tension of the polymers in solution.

Spreading Coefficient Calculation

Polymer blends.

The tendency of a liquid to spontaneously spread across a solid or liquid substrate can be expressed in terms of the surface interfacial tension of the components using Harkin's equation, described by W. D. Harkin, "The Physical Chemistry of Surface Films", page 23 (Reinhold Pub. Co., New York 1952).

1. $\lambda_{ij} = \gamma_j - \gamma_i - \gamma_{ij}$

Where $\gamma_j$ and $\gamma_i$ are the surface tension of the solid and liquid and $\gamma_{ij}$ is the interfacial tension of the solid liquid, and $\lambda_{ij}$ is the spreading coefficient. Spreading is predicted to occur only for positive values of lambda.

Harkin's equation can be rewritten for a system in which two dissimilar phases are dispersed within a third, by substituting the appropriate interfacial tensions for the surface tension values in eq. 1.

2. $\lambda_{31} = \gamma_{12} - \gamma_{32} - \gamma_{13}$

In this case, $\lambda_{31}$ is the spreading coefficient for component 3 on component 1 (conversely, $\lambda_{13}$ is the spreading coefficient for component 1 on component 3) and describes the physical situation in which the ability of one dispersed component to displace the matrix from the surface of a second component is considered. In an analogy with equation (1), envelope formation will be observed when lambda values are positive, and when $\lambda_{13}$ and $\lambda_{13}$ are both negative the dispersed phases will remain separated. Equation 2 can also be used to predict the behavior of polymer blends, using the method of S. Y. Hobbs, M. E. J. Dekkers and V. H. Watkins, in *Polymer*, Vol. 29, 1598–1602, (1988), and references cited therein, if the interfacial tension for various polymers are known.

Polymeric solutions or liquids.

Figure 5:
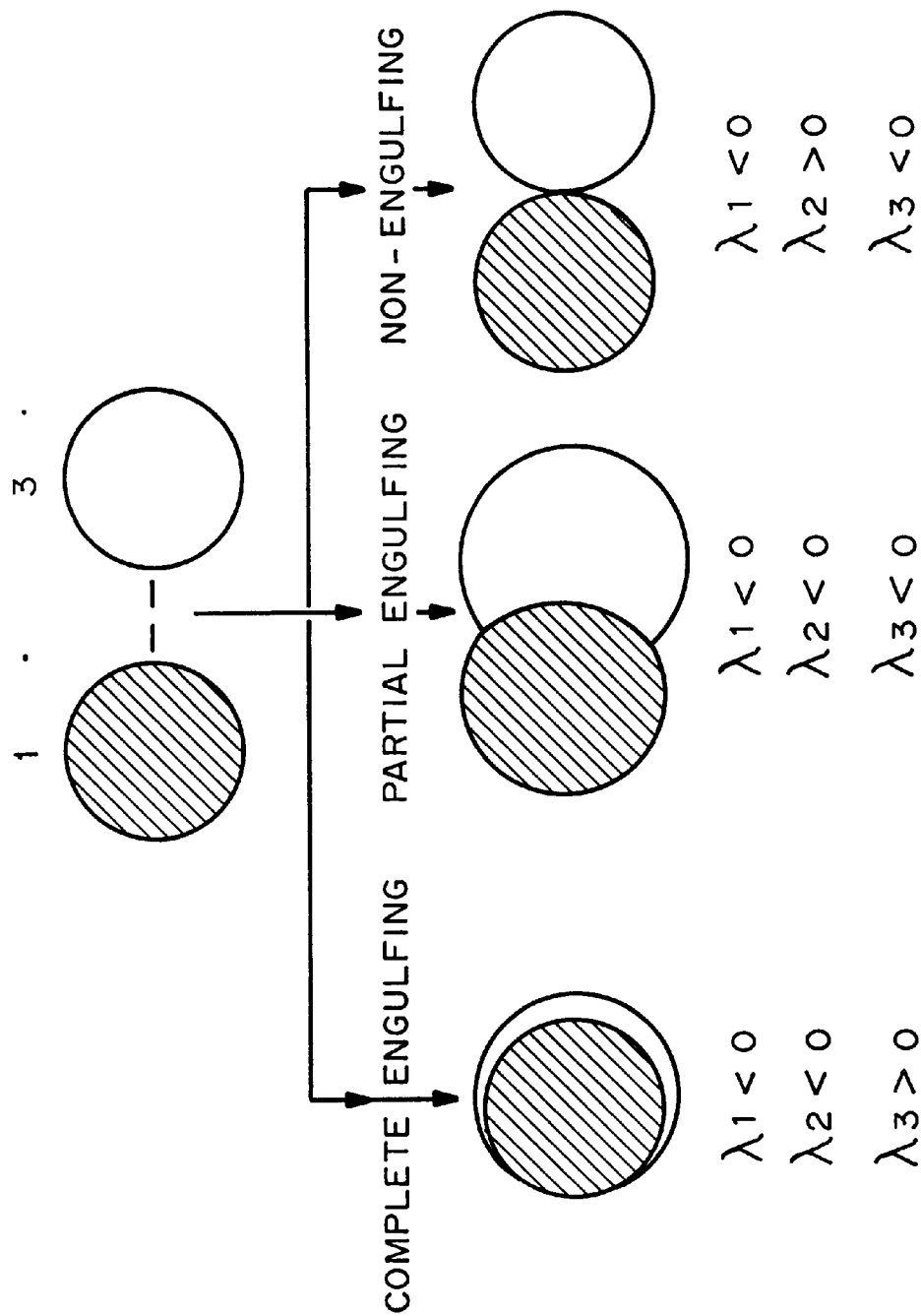
FIG. 5 is a schematic of the three ways in which two separate polymer phases can interact according to the method of the present invention.

The same equations can be applied when two immiscible liquid drops, designated as phase 1 and 3, and suspended in a third immiscible liquid, phase 2, are brought into contact. The resulting equilibrium configuration is readily predicted from the interfacial tension and the spreading coefficients. Three cases can be envisioned, as shown schematically in FIG. 5:

a) one polymer completely engulfing the other polymer, b) one polymer partially engulfing the other polymer, c) both polymer phases non-engulfing.

Based on this theory, it is possible to measure the interfacial tension, or calculate the interfacial tension, based on measurements of the surface tension of the polymers in solution, of the polymers which were described in the above examples and predict which polymer-solvent systems will yield multilayered microspheres. These results are summarized in Table 1.

The surface tension is measured using techniques known to those skilled in the art. The data in Table 1 was obtained using a Fisher Surface Tensiometer Model 20 according to the manufacturer's directions. The method employs du Nouy ring method and consists of a platinum ring of known diameter which in placed in the polymer solution, then slowly pulled vertically. The ring attaches to the surface of the liquid and resists detaching from the liquid. The force required to detach the ring from the surface of the liquid is measured and noted as apparent surface tension. This is multiplied by the correction factor, F, on page 8 of the Fisher Scientific instruction manual, to determine the real surface tension.

Interfacial tension for liquids is measured similarly. In a vessel, two liquids with different densities are carefully placed to avoid mixing. The platinum ring is slowly inserted until it is well inside the lower liquid. The ring is lightly shaken to ensure that it is devoid of any of the top layer liquid, using caution so as to not mix the liquids, especially at the interface. The apparatus is then set to determine the interfacial tension. The same procedure for determining surface tension is then followed, pulling the ring vertically until it breaks the surface of the bottom liquid and enters the liquid on the top.

TABLE I

Surface Interfacial Values of Polymer Solutions.

| Phases 1/2/3 | $lambda_{12}$ | $lambda_{13}$ | $lambda_{23}$ | $lambda_1$ | $lambda_2$ | $lambda_3$ |
|---|---|---|---|---|---|---|
| PLA/W/PS | 2.28 | 0 | 2.1 | -.17 | -4.39 | .17 |
| EVA/W/PS | 2.41 | 0 | 2.11 | 0.3 | -4.52 | .3 |
| PS/W/PA | 2.11 | 0 | .92 | -1.19 | -3.2 | 1.36 |
| PLA/W/PA1 | 2.28 | 0 | .92 | -1.36 | -3.2 | 1.36 |
| PLA/W/PA2 | 2.28 | 0 | 2.12 | -16 | -4.4 | .16 |

PLA is polylactic acid; PS is polystyrene; EVA is ethylene vinyl acetate; PA is a polyahydride; W is water.

It can be readily ascertained from this table by substituting into equations 1 and 2 that these systems should yield multilayered microspheres.

Modifications and variations of the method of the present invention will be obvious to those skilled in the art from the foregoing detailed description and examples. One skilled in the art will also be able to optimize the method of the present invention for particular polymer and substance mixtures from the foregoing detailed description of the invention and examples. It is intended that such modifications, variations, and optimizations will come within the scope of the appended claims.

We claim:

1. Polymeric microspheres formed of a first polymer, a second polymer, and a substance having a particle diameter of fifty microns or less incorporated throughout at least one of the polymers;

wherein the first polymer forms a solid spherical, polymeric core not having the substance as the core of the polymeric core;

wherein the polymeric core is coated with a single distinct layer of a uniform thickness of the second polymer; and wherein the first and second polymers are immiscible when melted or placed in a solvent and separate into distinct phases and the surface tension and interfacial tension of the polymers cause the second polymer to engulf the first polymer.

2. The microspheres of claim 1 wherein the first and second polymers are selected from the group consisting of polyanhydrides, polyorthoesters, polylactic acid polyglycolic acid, cellulose acetate, polystyrene, polyamides, ethylene vinyl acetate, polybutadiene, polyurethanes, and copolymers and blends thereof.

3. The microspheres of claim 1 wherein the first and second polymers are biodegradable and the substance is a drug.

4. The microspheres of claim 1 wherein the substance is incorporated into both layers.

5. Polymeric microspheres formed of a first polymer, a second polymer, and a substance having a particle diameter of fifty microns or less incorporated throughout at least one of the polymers, wherein the first polymer forms multiple spheres within a layer of the second polymer, the spheres not having the substance as the core of the polymeric core;

wherein the first and second polymers are immiscible when melted or placed in a solvent and separate into distinct phases and the surface tension and interfacial tension of the polymers cause one polymer to engulf the other polymer.

* * * * *